(12) United States Patent
Wimberger Friedl et al.

(10) Patent No.: US 12,051,203 B2
(45) Date of Patent: Jul. 30, 2024

(54) CALIBRATING RADIOLOGICAL DATA BASED ON CELL DISTRIBUTION

(71) Applicant: KONINKLIJKE PHILIPS N.V., Eindhoven (NL)

(72) Inventors: Reinhold Wimberger Friedl, Waare (NL); Vanda Lucia De Carvalho Vitorino De Almeida, Veldhoven (NL); Pedro Jorge Da Silva Rodrigues, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 340 days.

(21) Appl. No.: 17/419,751

(22) PCT Filed: Dec. 24, 2019

(86) PCT No.: PCT/EP2019/086998
§ 371 (c)(1),
(2) Date: Jun. 30, 2021

(87) PCT Pub. No.: WO2020/141137
PCT Pub. Date: Jul. 9, 2020

(65) Prior Publication Data
US 2022/0067939 A1    Mar. 3, 2022

(30) Foreign Application Priority Data

Jan. 3, 2019 (EP) .................. 19150208

(51) Int. Cl.
*G06T 7/00*       (2017.01)
*A61B 6/03*       (2006.01)
(Continued)

(52) U.S. Cl.
CPC ............ *G06T 7/0014* (2013.01); *A61B 6/032* (2013.01); *A61B 6/037* (2013.01); *A61B 6/50* (2013.01);
(Continued)

(58) Field of Classification Search
None
See application file for complete search history.

(56) References Cited

U.S. PATENT DOCUMENTS 5,281,517 A * 1/1994 Bacus .................... G06V 20/69
                                                    436/805
6,483,948 B1   11/2002 Spink
(Continued)

OTHER PUBLICATIONS

Nahrendorf, Matthias, et al. "Hybrid PET-optical imaging using targeted probes." Proceedings of the National Academy of Sciences 107.17 (2010): 7910-7915. (Year: 2010).*
(Continued)

*Primary Examiner* — Michelle M Entezari Hausmann

(57) ABSTRACT

Methods and systems for calibrating radiological data associated with a tissue in a subject are provide. Various embodiments described herein analyze a radiological image of the tissue to calculate a raw value indicative of a biological parameter such as metabolic activity in the tissue, and analyze a microscopy image of the tissue to identify a distribution of cells of interest within the tissue. A calibrated value indicative of a biological parameter (e.g. metabolic activity) of cells of interest within the tissue is then calculated, by correcting the raw value based on the identified distribution of cells of interest within the tissue.

20 Claims, 4 Drawing Sheets

(51) Int. Cl.
    *A61B 6/50*     (2024.01)
    *G06V 20/69*     (2022.01)

(52) U.S. Cl.
    CPC .... *G06V 20/69* (2022.01); *G06T 2207/10056* (2013.01); *G06T 2207/10081* (2013.01); *G06T 2207/10088* (2013.01); *G06T 2207/10104* (2013.01); *G06T 2207/10108* (2013.01); *G06T 2207/30024* (2013.01); *G06T 2207/30096* (2013.01)

(56) References Cited

U.S. PATENT DOCUMENTS

| | | | |
|---|---|---|---|
| 7,383,076 | B2 * | 6/2008 | Ntziachristos ..... G01N 21/6428 600/431 |
| 9,767,555 | B2 | 9/2017 | Madabhushi et al. |
| 2010/0121172 | A1 | 5/2010 | Ladic |
| 2012/0147010 | A1 * | 6/2012 | Schmidt ................ G06T 11/206 345/440 |
| 2014/0242600 | A1 | 8/2014 | Lei et al. |
| 2015/0087974 | A1 | 3/2015 | Black |
| 2015/0185204 | A1 | 7/2015 | Kuhn et al. |
| 2017/0071496 | A1 | 3/2017 | Gillies et al. |

OTHER PUBLICATIONS

Van de Plas, Raf, et al. "Image fusion of mass spectrometry and microscopy: a multimodality paradigm for molecular tissue mapping." Nature methods 12.4 (2015): 366-372. (Year: 2015).*

Pratx, Guillem, et al. "Radioluminescence microscopy: measuring the heterogeneous uptake of radiotracers in single living cells." ( 2012): e46285. (Year: 2012).*

Kinahal et al."PET/CT Standardized Uptake Values in Clinical Practice and Assessing Response to Therapy" Semin Ultrasound CT MR Dec. 2021 vol. 31 (6) p. 496-505.

Avril N, Menzel M, Dose J, Schelling M, Weber W, Janicke F, Nathrath W, Schwaiger M. Glucose metabolism of breast cancer assessed by 18F-FDG PET: histologic and immunohistochemical tissue analysis. J Nucl Med. Jan. 2001;42 (1):9-16. PMID: 11197987.

Yin et al. "Tumor Cell Load and Heterogeneity Estimation Form Diffusion-Weigted MRI Calibrated With Histological Data . . . " IEEE Transactions on Medical Imaging vol. 37, No. 1, Jan. 2018.

Takada et al, "Metabolic characteristics of programmed cell death-ligand 1-expressing lung cancer on 18F fluorodeoxyglucose positron emission tomography/computed tomography", Cancer Medicine 2017; 6(11):2552-2561, 10.1002/cam4.1215.

Lv et al, "Value of 18F-FDG PET/CT for predicting EGFR mutations and positive ALK expression in patients with non-small cell lung cancer: a retrospective analysis of 849 Chinese patients", EJNMMI 2017, Nov. 21, 2017, 10.1007/s00259-017-3885-z.

Moscoso et al, "Texture analysis of high-resolution dedicated breast 18F-FDG PET images correlates with immunohistochemical factors and subtype of breast cancer", EJNMMI 2017, 10.1007/s00259-017-3830-1.

Dubois et al. "Evaluation of Hypoxia in an Experimental Rat Tumor Model by [18F] Fluoromisonidazole PET and Immunohistochemistry" British Journal of Cancer (2004) 91 p. 1947-1954.

Search Report and Written Opinion From PCT/EP2019/086998 dated Jul. 9, 2020.

* cited by examiner

CALIBRATING RADIOLOGICAL DATA BASED ON CELL DISTRIBUTION

CROSS REFERENCE TO RELATED APPLICATIONS

This application is a U.S. national phase application of International Application No. PCT/EP2019/086998 filed on Dec. 24, 2019, which claims the benefit of EP Application Ser. No. 19150208.7 filed on Jan. 3, 2019 and is incorporated herein by reference.

FIELD OF THE INVENTION

Embodiments described herein generally relate to methods, systems and computer program products for calibrating radiological data associated with a tissue in a subject, for instance measurements indicative of a biological parameter (e.g. metabolic activity) in the tissue obtained by methods such as positron emission tomography (PET) imaging. The methods are particularly applicable to correcting such radiological data in order to provide calibrated values useful in clinical decision making, e.g. for determining a prognosis or predicting response to a therapy for cancer.

BACKGROUND OF THE INVENTION

The TCA cycle is a critical metabolic pathway that allows mammalian cells to utilize glucose, amino acids, and fatty acids. The entry of these fuels into the cycle is carefully regulated to efficiently fulfil the cell's bioenergetics, biosynthetic, and redox balance requirements. Cancer cells, in comparison with normal cells, exhibit distinctive physiopathology, including: (a) autonomous mechanisms of cell growth, (b) divergence from the factors involved in growth inhibition, (c) evasion from anoikis, immune-surveillance and apoptosis, (d) evolutionary regulation of growth, (e) invasiveness and metastatic colonization.

To carry out replicative division, a cell must duplicate its genome, proteins and lipids and assemble these elements into daughter cells. The increased rate of cell division in cancer requires metabolic pathways to be redesigned, leading to a rise in tumor cell metabolism. Reprogramming of glucose metabolism is a key event in tumorigenesis. Tumor cells undergo a metabolic switch from oxidative phosphorylation (OXPHOS) to glycolysis in which a molecule of glucose is degraded to two molecules of pyruvate. Depending on the supply of oxygen for the cells, pyruvate is either reduced to lactate in the absence of oxygen via an anaerobic glycolysis pathway, or oxidized to yield acetyl-coenzyme A in the presence of oxygen and then oxidized completely to $CO_2$ and $H_2O$ via citric acid cycle. The majority of tumor cells depend on high rates of glycolysis for growth and survival, even when there is sufficient oxygen. This type of aerobic glycolysis is called the Warburg effect.

To support this continuous cell proliferation, the biosynthetic capabilities of tumor cells are increased, including fatty acid and nucleotide synthesis. In contrast, b-oxidation of fatty acids is suppressed and futile cycles are minimized. These changes increase the metabolic autonomy of the transformed cells, allowing them to acquire an enhanced anabolic phenotype.

Various radiological methods may be used to monitor metabolic activity in tumors. For instance, PET scanning with the tracer fluorine-18 (18-F) fluorodeoxyglucose (FDG), called FDG-PET, is widely used in clinical oncology. This tracer is a glucose analog that is taken up by glucose-using cells and phosphorylated by hexokinase (whose mitochondrial form is greatly elevated in rapidly growing malignant tumors). The typical administrated 18F-FDG activity used in an oncological scan are in the range of 200-450 MBq. Because the oxygen atom that is replaced by F-18 to generate FDG is required for the next step in glucose metabolism in all cells, no further reactions occur in FDG. Furthermore, most tissues (with the notable exception of liver and kidneys) cannot remove the phosphate added by hexokinase. This means that FDG is trapped in any cell that takes it up, until it decays, since phosphorylated sugars, due to their electrical charge, cannot exit from the cell. This results in intense radiolabeling of tissues with high glucose uptake, such as the brain, the myocardium, the liver, and most cancers. As a result, FDG-PET can be used for diagnosis, staging, treatment planning and monitoring treatment of cancers, particularly in Hodgkin's lymphoma, non-Hodgkin lymphoma, breast, melanoma, and lung cancer.

Using radiological methods such as PET imaging to determine the metabolic activity of tumors is well established and signal intensities, as expressed in Standard Uptake Values (SUV) are used for staging and prognosis of cancer. The signal is higher in tumors as compared to the surrounding tissue due to the metabolic activity of cancer cells in the tumor. However, the SUV values also depend on the cell density within the tissue. In addition, tumors do not contain only cancer cells. Non-tumor cells are also present, including immune effector cells such as T cells that are directed against the tumor. Since the cell density can vary and effector immune cells and other metabolically active non-tumor cells can contribute to the FDG-PET signal, the metabolic activity of the tumor cells cannot necessarily be directly inferred from the FDG-PET signal. Moreover since radiological methods such as PET imaging lack cellular resolution the FDG-PET signal cannot be used on its own to discriminate between metabolic activity of different cell types within a tissue.

A need exists, therefore, for methods and systems that are capable of calibrating radiological image data in order to determine a biological parameter (e.g. metabolic activity) of cells of interest within a tissue.

SUMMARY OF THE INVENTION

In one aspect, embodiments relate to a method for calibrating radiological data associated with a tissue in a subject. The method includes analyzing a radiological image of the tissue to calculate a raw value indicative of a biological parameter in the tissue; analyzing a microscopy image of the tissue to identify a distribution of cells of interest within the tissue; and calculating a calibrated value indicative of the biological parameter of cells of interest within the tissue, wherein the calibrated value is obtained by correcting the raw value based on the identified distribution of cells of interest within the tissue.

In some embodiments, the biological parameter is metabolic activity. Thus the method may comprise calculating a raw value indicative of metabolic activity in the tissue, and calculating a calibrated value indicative of metabolic activity in cells of interest within the tissue. In an alternative embodiment, the biological parameter may be expression of a cellular marker, e.g. a cell surface marker such as PD-L1. In such an embodiment, the method may comprise calculating a raw value indicative of expression of the marker in the tissue, and calculating a calibrated value indicative of expression of the marker in cells of interest within the tissue.

In some embodiments, the method comprises a step of analyzing the radiological image of the tissue to calculate raw values indicative of the biological parameter (e.g. metabolic activity) at a plurality of locations in the tissue. The method may further comprise associating the plurality of locations in the tissue with the distribution of the cells of interest identified by analyzing the microscopy image. In this embodiment, the method may further comprise calculating calibrated values indicative of the biological parameter (e.g. metabolic activity) of cells of interest at the plurality of locations in the tissue, wherein the calibrated values are obtained by correcting the raw values based on the identified distribution of cells of interest at each of the plurality of locations in the tissue.

In one embodiment, the method further comprises modifying the radiological image to show the calibrated values indicative of the biological parameter (e.g. metabolic activity) of cells of interest at the plurality of locations in the tissue.

In one embodiment, the tissue is suspected to comprise cancer cells. For instance, the cells of interest may comprise cancer cells and/or effector T cells.

In particular embodiments, the radiological image may be obtained by positron emission tomography (PET), computerized tomography (CT), magnetic resonance imaging (MRI) and/or single-photon emission computed tomography (SPECT). In one embodiment, the raw value indicative of metabolic activity in the tissue is a standard uptake value (SUV) obtained by PET imaging using (18-F) fluorodeoxyglucose (FDG). See e.g. Paul E Kinahan et al in "PET/CT Standardized Uptake Values (SUVs) in Clinical Practice and Assessing Response to Therapy", Semin Ultrasound CT MR, December 2010 December, vol 31(6), pp 496-505.

In some embodiments, the raw value indicative of the biological parameter can be calculated based on data from two or more imaging modalities. For instance, radiological data and/or images obtained by any combination of positron emission tomography (PET), computerized tomography (CT), magnetic resonance imaging (MRI) and/or single-photon emission computed tomography (SPECT) may be analyzed to calculate the raw value indicative of the biological parameter.

In one embodiment, the raw value indicative of the biological parameter is calculated by analyzing a combination of images obtained by PET (e.g. providing metabolic activity) and contrast-enhanced perfusion CT (e.g. providing information on angiogenesis and blood-flow characteristics in tumors). In specific embodiments, CT perfusion data (e.g. blood flow (BF), blood volume (BV) and Mean Transit Time (MTT)) is obtained by an analysis of the time-contrast enhancement curve. In one embodiment, perfusion status of the tissue can also be derived from MR images.

In one embodiment, the radiological image is obtained by PET. In some such embodiments, the biological parameter calculated from the PET image may relate to a biological process other than metabolic activity. For instance, specific PET tracers may be used to provide PET images from which specific biological parameters can be calculated. In particular embodiments, the biological parameter may relate to: 1) a level of PD-L1 expression in the tissue, e.g. measured with an antibody PD-L1 PET tracer; 2) a level of tumor-cell infiltrating lymphocytes (e.g. CD8+, CD4+ T cells) in the tissue, e.g. measured with an appropriate tracer; 3) a level of tumour cell proliferation in the tissue, e.g. measured with 18F-fluorothymidine (18F-FLT); or 4) a level of tumour cell hypoxia in the tissue, e.g. measured with an appropriate tracer such as 18F-fluoromisonidazole (18F-FMISO).

In one embodiment, the microscopy image is obtained by histochemical and/or immunohistochemical staining of a biopsy or resected tissue sample from the tissue.

In one embodiment, the method comprises calculating a density of cells of interest in the tissue from the cell distribution identified by analyzing the microscopy image, and calculating the calibrated value indicative of the biological parameter (e.g. metabolic activity) of cells of interest by correcting the raw value based on the cell density.

In some embodiments, the cells of interest may be identified based on expression of one or more protein markers, e.g. cancer cell and/or immune cell markers. In one embodiment, the cells of interest comprise cancer cells that overexpress programmed death-ligand 1 (PD-L1).

According to another aspect, embodiments relate to a system for calibrating radiological data associated with a tissue in a subject. The system includes an interface for receiving a radiological image of the tissue and a microscopy image of the tissue; a memory; and a processor configured to execute instructions stored on the memory to (i) calculate a raw value indicative of the biological parameter (e.g. metabolic activity) in the tissue from the radiological image; (ii) to identify a distribution of cells of interest within the tissue from the microscopy image; and (iii) calculate a calibrated value indicative of the biological parameter (e.g. metabolic activity) of cells of interest within the tissue, by correcting the raw value based on the identified distribution of cells of interest within the tissue.

According to another aspect, embodiments relate to a computer program product comprising a non-transitory computer readable medium, the computer readable medium having computer readable code embodied therein, the computer readable code being configured such that, on execution by a suitable computer or processor, the computer or processor is caused to perform the method as defined herein.

BRIEF DESCRIPTION OF DRAWINGS

Non-limiting and non-exhaustive embodiments of the invention are described with reference to the following figures, wherein like reference numerals refer to like parts throughout the various views unless otherwise specified.

DETAILED DESCRIPTION OF EMBODIMENTS

Figure 1:
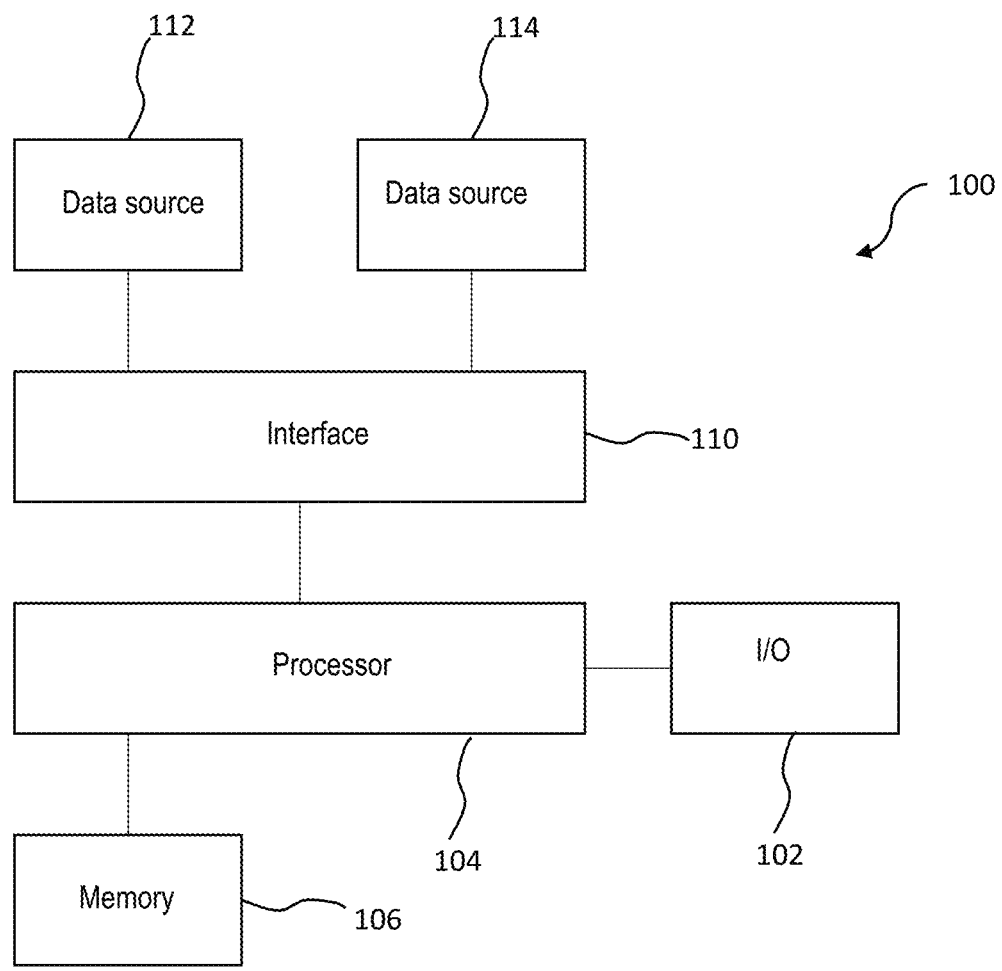
FIG. 1 illustrates a system for calibrating radiological data associated with a tissue in a subject in accordance with one embodiment.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

FIG. 1 illustrates a system 100 for calibrating radiological data associated with a tissue in a subject in accordance with one embodiment.

The system 100 may include a user input/output (I/O) device 102 and a processor 104 executing instructions stored on memory 106. The processor 104 may be in communication with or otherwise include an interface 110 for receiving imaging data from image data sources 112 and 114. For instance image data source 112 may comprise a radiological imaging system such as a PET scanner, whereas image data source 114 may comprise a microscopy imaging system, such as a digital microscope.

The I/O device 102 may be any suitable device that can receive commands from an operator and output radiological and imaging data. The I/O device 102 may be configured as, for example but without limitation, a personal computer, a tablet, laptop, mobile device, or the like.

The processor 104 may be any specifically configured processor or hardware device capable of executing instructions stored on memory 106 to process radiological and microscopy imaging data in order to determine quantitative values therefrom. The processor 104 may include a microprocessor, a field programmable gate array (FPGA), application-specific integrated circuit (ASIC), or other similar device. In some embodiments, such as those relying on one or more ASICs, the functionality described as being provided in part via software may instead be hardwired into the operation of the ASICs, and as such, any associated software may be omitted.

The memory 106 may be L1, L2, L3 cache or RAM memory configurations. The memory 106 may include non-volatile memory such as flash memory, EPROM, EEPROM, ROM, and PROM, or volatile memory such as static or dynamic RAM, as discussed above. The exact configuration/type of memory 106 may of course vary as long as instructions for analyzing radiological and microscopy imaging data can be executed by the processor 104.

The interface 110 may receive radiological imaging data from the data source 112 and microscopy imaging data from data source 114. The interface 110 may then communicate the received data to the processor 104 for analysis. The radiological and microcopy imaging data is typically in the form of digital images of a tissue of interest within the subject.

The processor 104 is configured to calculate a raw value indicative of metabolic activity in the tissue from the radiological image, and to identify a distribution of cells of interest within the tissue from the microscopy image. The processor 104 then calculates a calibrated value indicative of metabolic activity of cells of interest within the tissue, by correcting the raw value based on the identified distribution of cells of interest within the tissue.

After analysis of the received data, the processor 104 may output calibrated values indicative of metabolic activity of cells of interest within the tissue to the I/O device 102 or another display unit. In some embodiments, the output may be in the form of a modified radiological image showing calibrated values indicative of metabolic activity of cells of interest at a plurality of locations in the tissue.

Figure 2:
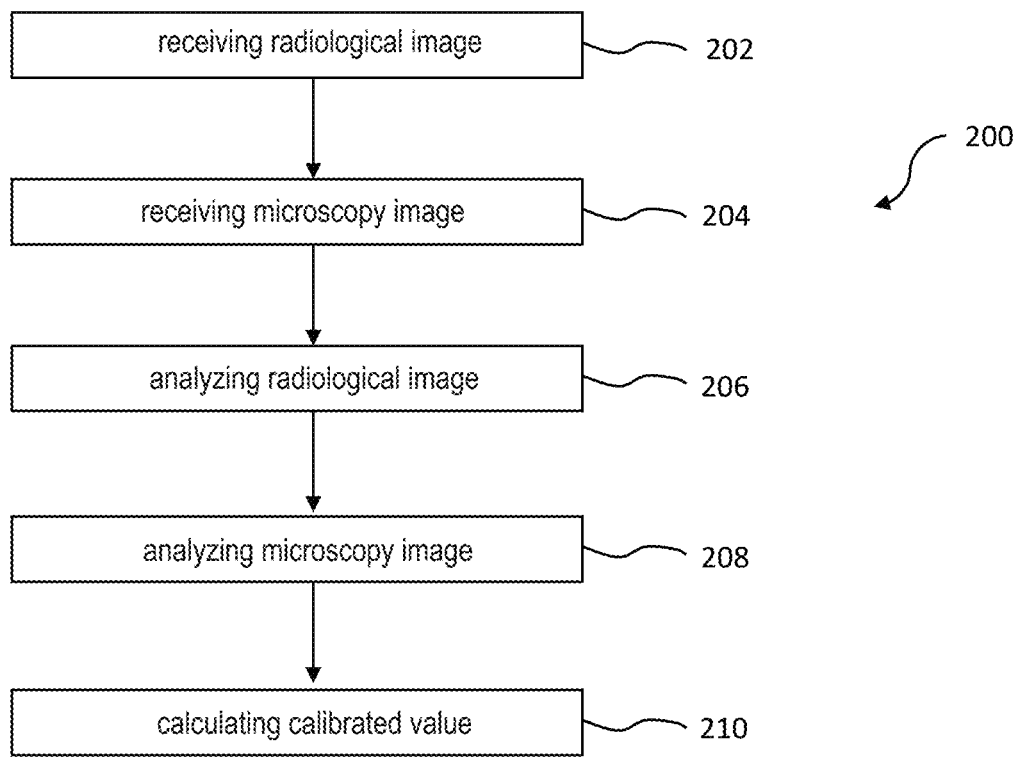
FIG. 2 depicts a flowchart of a method for calibrating radiological data associated with a tissue in a subject using the system of FIG. 1 in accordance with one embodiment.

FIG. 2 depicts a flowchart of a method 200 for calibrating radiological data associated with a tissue in a subject using the system of FIG. 1 in accordance with one embodiment. Step 202 involves receiving a radiological image of a tissue, e.g. a PET image. Step 204 involves receiving a corresponding microscopy image of the tissue, e.g. a digital light microscopy image. "Image" as used herein should be construed broadly, to include not only a whole array of image signals but, in an extreme case, a single image signal for a single voxel position or a selection of such image signals for a sub-set of voxel positions in the whole field of view.

The radiological and microscopy images may be received by the interface 110 from the radiological imaging system 112 and microscopy imaging system 114. A processor such as the processor 104 of FIG. 1 may receive these images from the interface 110 of FIG. 1. In alternative embodiments, the radiological and microscopy images may be transmitted to the interface 110 and/or processor 104 by the I/O device 102, e.g. where the images are stored in another location after image acquisition by imaging systems.

Step 206 involves analyzing the radiological image of the tissue to calculate a raw value indicative of metabolic activity in tissue. The value indicative of metabolic activity may be, for example, a standard uptake value (SUV). For instance, the SUV may be obtained by PET imaging using (18-F) fluorodeoxyglucose (FDG). In some embodiments, the raw value (e.g. SUV) may be calculated as an average or mean value over a defined volume of the tissue. In such embodiments, a defined volume of tissue in the sample is represented by a single value indicative of metabolic activity. In alternative embodiments, the radiological image may be analyzed to calculate raw values at a plurality of locations in the tissue. In these embodiments, the raw values at various locations in the tissue may be represented visually by an image showing the distribution of values (e.g. SUVs) across the tissue.

Step 208 involves analyzing the microscopy image of the tissue to identify a distribution of cells of interest within the tissue. For instance, the processor 104 may use an algorithm suitable for analysis of digital microscopy images to identify stained objects within the tissue such as cell nuclei. The method may therefore identify all cells present within the image, or a subset of cells. In some embodiments the image is analyzed to identify a subset of cells such as cancer cells and/or immune cells such as effector T cells. Individual cell types may be identified based on expression of characteristics markers, e.g. proteins which are stained in the image by immunohistochemical processing of the tissue sample.

Once the distribution of cells of interest in the tissue has been identified, the density of cells of interest in the tissue can be calculated. Moreover the processor 104 may associate particular locations in the tissue having specific raw values (SUVs) with the identified cell distribution.

Step 210 involves calculating a calibrated value indicative of metabolic activity of cells of interest within the tissue. The processor 104 may calculate the calibrated value by correcting the raw value based on the identified distribution of cells of interest within the tissue. For instance, the mean SUV obtained for a defined volume of the tissue may be normalized to the determined cell density (of total cells or specific cells of interest such as cancer cells). Typically this means that the mean SUV is divided by a factor indicative of the density of cells of interest. Thus, for instance, a high SUV value may be corrected to a lower calibrated value based on a high density of cells of interest within the tissue.

In embodiments where raw values indicative of metabolic activity at a plurality of locations in the tissue are calculated, calibrated values (e.g. of SUV) at each location may be determined. For instance, since each location in the original radiological image can be associated with the identified cell distribution, the raw value (e.g. SUV) at each location can be corrected based on the distribution of cells of interest at that location. The original radiological image can then be modified to show the calibrated values, which may be outputted via the I/O device 102 or a display.

The radiological image (e.g. as analyzed in step 206 shown in FIG. 2) may be obtained by any suitable radiological imaging method, for example, by positron emission tomography (PET), computerized tomography (CT), magnetic resonance imaging (MM) and/or single-photon emission computed tomography (SPECT). Typically, the image is a PET image.

The value indicative of metabolic activity in the tissue, e.g. determined by PET imaging, is typically an SUV. However the correlation/calibration step can be applied to different measures derived from the PET images e.g. SUVmax, SUVmean, Metabolic Tumor Volume (MTV), Total Lesion Glycolysis (TLG), or other, high-order, so-called radiomics features. "Metabolic activity" as used herein includes chemically transforming (or processing) certain chemical compounds ("metabolites") by a cell of the human or animal body. One important but non-limiting example is the transformation of glucose to obtain energy.

In other embodiments, step 206 of the method may involve analyzing the radiological image of the tissue to calculate a raw value indicative of a biological parameter other than metabolic activity in tissue. In general, the biological parameter may relate to any process that can be assessed by a functional or anatomic diagnostic imaging technique, in particular radiological imaging methods. For instance, specific PET tracers may be used to determine the values of specific biological parameters in the tissue. Some (non-exhaustive) examples are given: 1) a raw value indicative of PD-L1 expression in the tissue may be determined from a PET image obtained using an anti-PD-L1 antibody PET tracer (e.g. 89Zr-atezolizumab, 18F-BMS-986192; 2) a raw value indicative of a level of tumor-cell infiltrating lymphocytes (e.g. CD8+, CD4+ T cells) in the tissue may be determined from a PET image obtained with an appropriate antibody PET tracer (e.g. 89Zr-Df-IAB22M2C); 3) a raw value indicative of tumour cell proliferation in the tissue may be determined from an image obtained using 18F-FLT PET imaging; 4) a raw value indicative of tumour cell hypoxia may be calculated from an image obtained with appropriate tracer (e.g. using 18F-FMISO PET imaging).

The methods described herein involve (e.g. in step 208 shown in FIG. 2) a step of analyzing a microscopy image of the tissue. The microscopy image is typically a digital light microscopy image, e.g. obtained by a digital microscope. The microscopy image shows the same tissue which is the subject of the radiological image, e.g. the microscopy image is of a tissue specimen obtained from a biopsy or resected tissue sample taken from the subject who has been imaged using e.g. PET.

The tissue specimen (e.g. obtained by biopsy or resection from a subject) can be prepared using known techniques for light microscopy analysis and imaging. For instance, haemotoxylin and eosin (H&E) staining of paraffin-embedded sections is the default technology to visualize tissue on a glass slide for pathology analysis. Immunohistochemistry (IHC) staining is a well-known approach to identify overexpression of proteins on cells in pathology tissue slides. The staining results in a typical brown appearance of tissue where the targeted protein is overexpressed as compared to normal. For example, by using an antibody against programmed death ligand 1 (PD-L1), its overexpression can be detected. The result is typically indicated as a so-called proportionality score, i.e. the percentage of tumor cells that are designated as positive (above threshold).

3D images can be obtained from the biopsy or resected tissue material, with or without staining, in order to provide an intermediate 3D representation of the morphology of the biopsy before processing in paraffin and micro-toming into thin microscopy sections for pathology image acquisition. This can be done for example by optical coherence tomography, X-ray, and or multifocal microscopy after clearance of the tissue with an index matching substance.

The detection of features in pathology slides may be performed using known computer algorithms which can analyse digital images of the slides. For instance, convolutional neural networks may be trained by providing annotated data sets of pathology images where the objects of interest have been annotated manually by a pathologist. Such objects can be for instance cell nuclei. Also the classification of cell nuclei into for instance tumor cells or immune cells can be trained successfully. Thus in particular embodiments, deep learning computer algorithms may be trained and/or used to detect cell nuclei on digital images of tissue, and even discriminate between tumor and non-tumor tissue.

Computer-based detection algorithms may also be used in combination with IHC to detect cells of interest (e.g. overexpressing a particular protein) automatically. For instance, the presence and abundance of cells that are classified as being positive for the overexpression of PD-L1 in IHC images can be determined. Using computer-based detection enables true quantification of the number and density of objects in a region of interest, like a tumor lesion.

Figure 3:
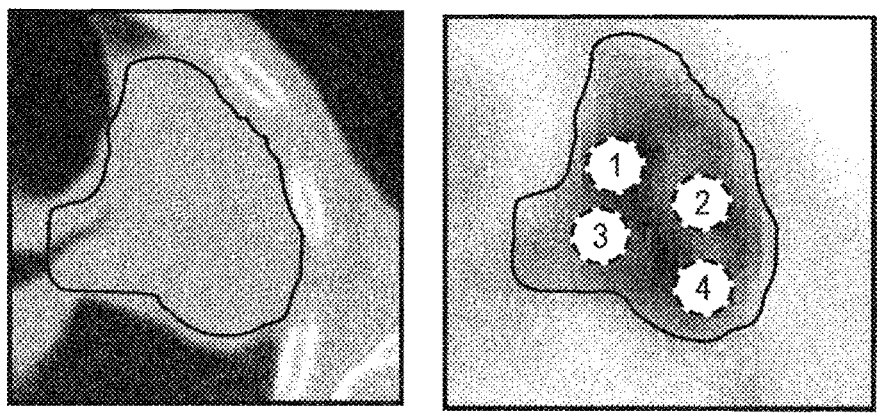
FIG. 3 depicts (A) a CT image of a tumor lesion and (B) a PET image of a tumor lesion analyzed in accordance with one embodiment.

FIG. 3 illustrates a further aspect of one embodiment of the present method. In a first step, a CT image (FIG. 3A) and a FDG-PET image (FIG. 3B) of a tissue in a subject are acquired. The image is analyzed firstly to identify the location of a tumor lesion present within the tissue (outline shown in FIGS. 3A and B). Secondly, the position of biopsy (e.g. core needle biopsy) or resection positions within the PET image is identified (locations 1 to 4 shown in FIG. 3B). SUV values for voxels in the PET image corresponding to the biopsy positions are then calculated.

A biopsy sample obtained from an identified location (e.g. a core needle biopsy sample obtained from a position corresponding to a defined location in the PET image, as described above) is processed using standard histological and/or immunohistochemical techniques to produce a slide for microscopic analysis. A light microscopy image of the slide is acquired by a digital microscope. The image is then processed to detect and classify cellular nuclei identified within the image. This allows the determination of a two-dimensional distribution of a particular cell type of interest (e.g. cancer cells). The two-dimensional distribution may be extrapolated to a 3D cell distribution and averaged to correspond to the voxel size of the PET image.

In the next step, for each voxel in the PET image the SUV values are corrected based on the cell distribution determined from the microscopy image. For instance, the SUV for each voxel obtained by PET is scaled by a factor correlating with the determined cell density (e.g. cancer cell density) for that voxel to obtain a calibrated SUV for each voxel. A modified PET image is then outputted showing the calibrated SUVs at each location in the tissue.

Figure 4:
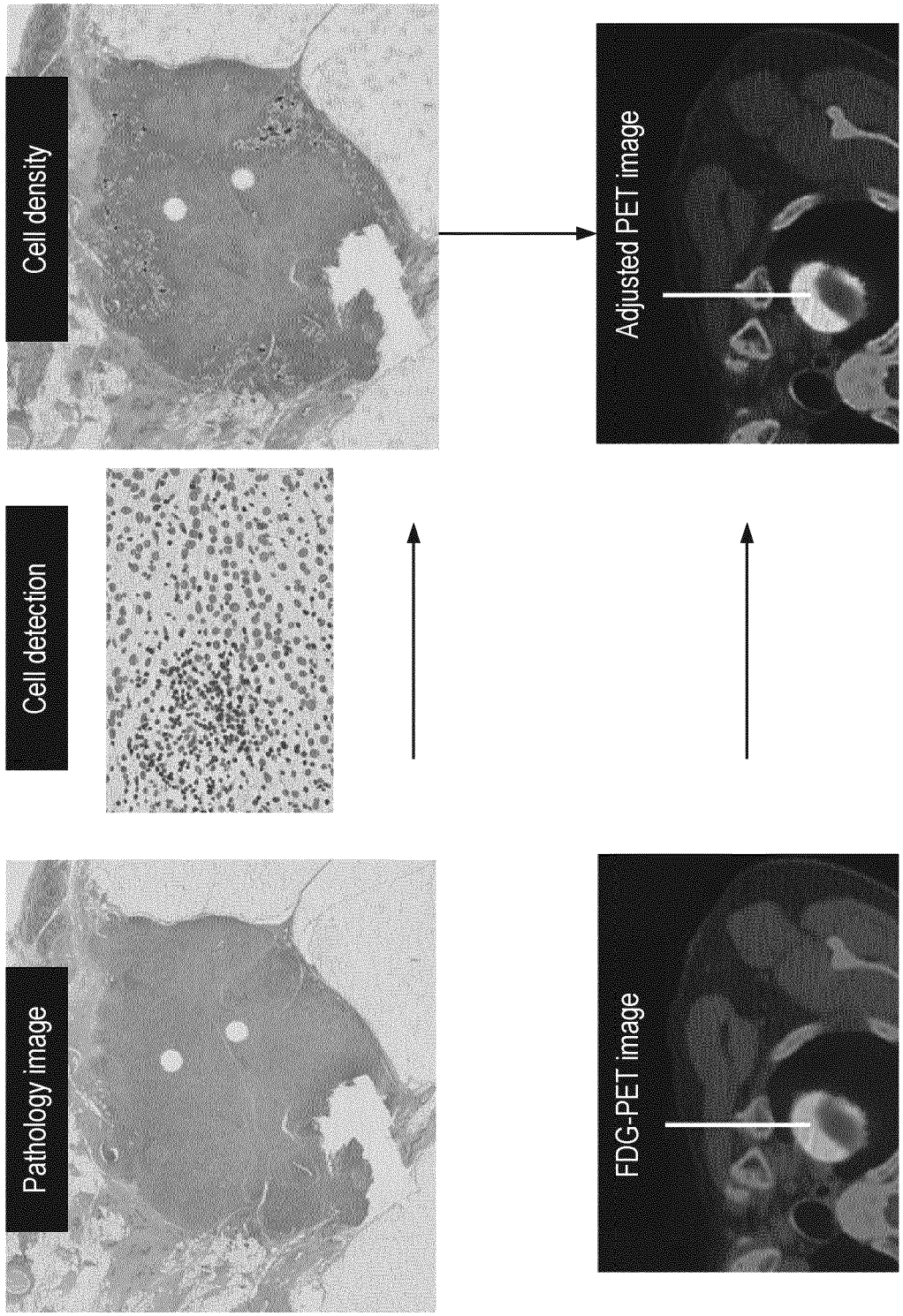
FIG. 4 depicts a method in accordance with one embodiment in which SUVs in an FDG-PET image of a tissue are corrected for the density of infiltrating effector T cells.

FIG. 4 illustrates a further aspect of an embodiment of the present method. In the method shown in FIG. 4, a pathology (i.e. light microscopic) image of a tissue derived from a tumor biopsy is obtained. The tissue sample has been stained using immunohistochemistry (IHC) to identify effector T cells. For instance, the effector T cells may be labelled with an antibody directed against an effector T cell surface marker such as CD8. The microscopy image is processed to detect staining representative of effector T cells, thereby determining the distribution of effector T cells within the tissue and enabling the density of infiltrating effector T cells at each location in the tumor to be calculated.

An FDG-PET image of the tissue covering the location of the biopsy is also obtained. The FDG-PET image provides a representation of SUVs at various locations in the tissue, which is indicative of metabolic activity at each location. The locations in the FDG-PET image are then associated with their corresponding positions in the microscopy image. The raw SUVs obtained for each voxel in the FDG-PET image are then scaled based on a factor proportional to the determined density of effector T cells at that position. The FDG-PET image is thus adjusted to represent calibrated SUVs at each location in the tissue sample, which are indicative of the level of metabolic activity of infiltrating effector T cells at each position.

Figure 5:
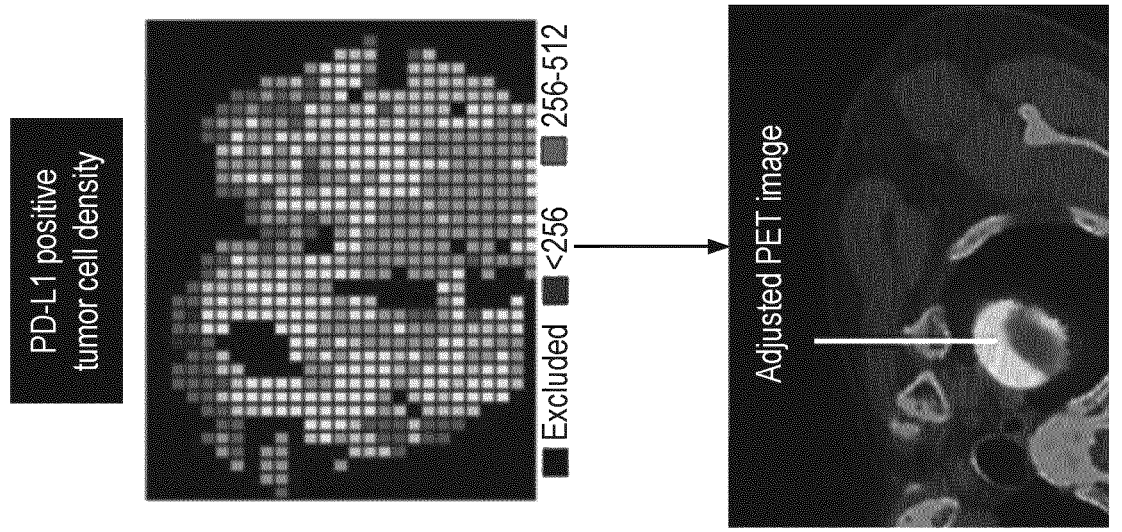
FIG. 5 depicts a method in accordance with one embodiment in which SUVs in an FDG-PET image of a tissue are corrected for the density of PD-L1 positive tumor cells.
Figure 5:
Figure 5:
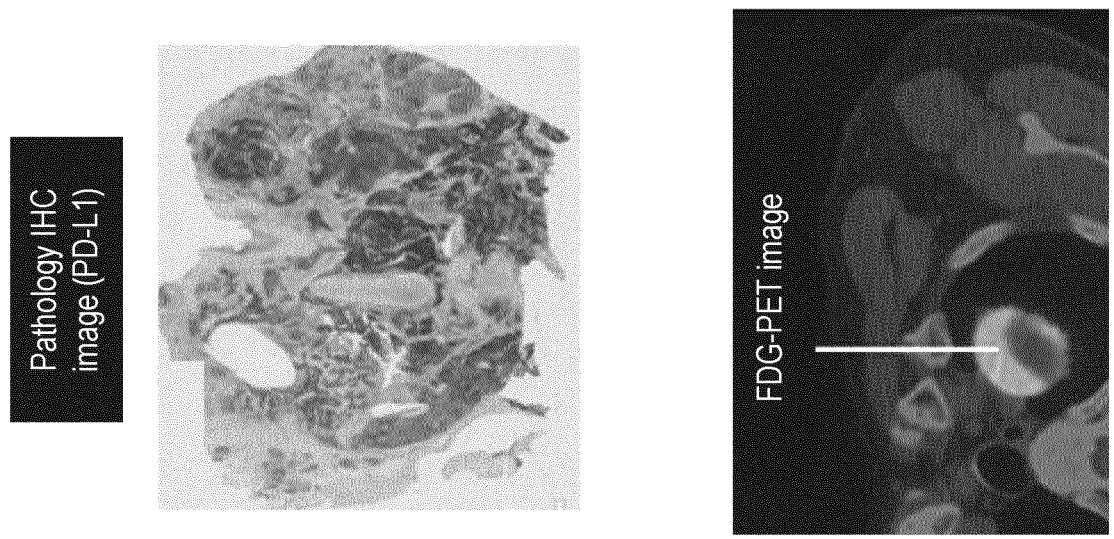

FIG. 5 illustrates a further aspect of an embodiment of the present method, that is similar in principle to that shown in FIG. 5 except that the FDG-PET SUVs are corrected based on the density of PD-L1 positive tumor cells (rather than effector T cells). In the method shown in FIG. 5, a tissue section from a tumor biopsy is stained by IHC using an antibody against PD-L1. A light microscopy image of the tissue is then processed to detect PD-L1-positive tumor cells, thereby enabling the density of PD-L1-positive tumor cells at each location in the tumor to be calculated.

An FDG-PET image of the tissue covering the location of the biopsy is also obtained. The raw SUVs obtained for each voxel in the FDG-PET image are then scaled based on a factor proportional to the determined density of PD-L1-positive tumor cells at each position in the tissue. The FDG-PET image is thus adjusted to represent calibrated SUVs at each location in the tissue sample, which are indicative of the level of metabolic activity of PD-L1-positive tumor cells at each position.

The methods described herein, especially e.g. with reference to FIG. 4 and FIG. 5, are particularly applicable to cancer diagnosis, prognosis and predicting responsiveness to therapy, e.g. immunotherapy with checkpoint inhibitors. Checkpoint inhibition immunotherapies (CIT), which are treatments that modulate the immune system, have become an important class of therapy for cancer, with FDA approvals for many cancer types even in 1st line. These therapies can achieve durable responses in late stage patients. However, the percentage of responders is, depending on the cancer type, only between 15 and 30% for monotherapy. Another characteristic of checkpoint blockade therapy is the late time point where response becomes evident.

The basic mechanism of CIT is the activation of cytotoxic T cells which are able to recognize the tumor as foreign. By blocking the checkpoint molecules on the target cells the effector function can be engaged and tumor cells can be killed by the infiltrating T cells. The clinically most important checkpoint is the programmed death 1/programmed death ligand 1 (PD-1/PD-L1). Overexpression of the PD-L1 molecule on tumor cells is used as biomarker for patient selection in NSCLC first line therapy in the US. However, it has become clear that the biomarker is not a good predictor of the response of a patient. A possible reason is the strong spatial and temporal heterogeneity of the expression of this biomarker which limits the validity of a determination on a small biopsy at a single time point.

PD-L1 is a signature of increased metabolic activity of the tumor cells. However immune cells such as effector T cells can also contribute to the metabolic activity detected using existing methods such as FDG-PET scanning. Therefore using known methods it is not possible to quantitatively relate the FDG-PET signal to the PD-L1 overexpression of the tumor cells.

By correcting the SUV values for effective cell densities and optionally cellular characteristics (e.g. cell type, protein overexpression, or genetic mutations) as derived from pathology the correlation with prognosis and/or response to therapeutic interventions should improve, making radiology a more powerful tool in the clinic. For instance, the SUV value can be related to the density of cancer cells and/or the combined densities of cancer cells and effector T cells. The SUV value normalized to cellular density can then be used for clinical decision making, for instance for prognosis of the patient or prediction of response to a therapy. Alternatively, the SUV-derived score is correlated to the density of PD-L1 overexpressing cancer cells in the tumor as determined from an IHC image of the tissue.

In particular, correlations to e.g. the calibrated values determined herein can be established in cohorts of patients and organs and related to prediction of prognosis and response to therapy, in particular response to immune therapy, as well as for monitoring the response to therapy. Once a correlation has been established to particular calibrated values the present method can be used for quality control as well.

In further embodiments, the radiological image data can be further calibrated using additional inputs (in addition to light microscopy (i.e. pathology) images). For instance, CT- and MRI-derived images can be used to further improve the understanding of the micro-environment or improve the spatial correlation of the pathology and radiology images. Morphological correlations in the CT or MR images and the pathology images can be used for extrapolation of pathology information outside the volume covered by the biopsy. In one embodiment, CT is combined with PET in order to allow better image registration. In another embodiment, the morphological features in the CT image can be used for alignment of images from pathology.

The raw value determined from the radiological (e.g. PET) image can also be combined with a perfusion parameter derived from a contrast-enhanced perfusion CT image (e.g. providing information on angiogenesis and blood-flow characteristics in tumors). CT perfusion data (e.g. blood flow (BF), blood volume (BV) and Mean Transit Time (MTT)) is obtained by an analysis of the time-contrast enhancement curve. In one embodiment, perfusion status of the tissue can also be derived from MR images.

Other embodiments may use image-guided biopsy methods in order to identify and store the coordinates of the biopsy location more accurately. Such methods may assist in associating particular locations in the radiology image with their corresponding locations in the microscopy (pathology) image, and thus the distribution of cells at such locations. In one embodiment, the radiological (e.g. PET) image is acquired before taking the biopsy sample. In such an embodiment, the biopsy can be guided to the position of the maximum (non-pathology corrected) SUV, within the lesion of interest that is targeted. In this way it is possible to correct the SUVmax, which is the most significant parameter for clinical decision making. The corrected SUV may be reported together with an associated confidence level that takes into account uncertainty related to the level of biopsy/ resection to PET/CT image co-registration.

In further embodiments, the present method is employed to calibrate radiological image data related to biological parameters other than metabolic activity. For instance, in one embodiment the method may be used to calibrate radiological data indicative of expression of e.g. a cell surface marker such as PD-L1. For instance, molecular probes for PET or SPECT, such as anti-PD-L1 radiotracers, can be used to generate radiology images indicative of the density of PD-L1 expression in a tumor. Since PET and SPECT lack cellular resolution, this PD-L1 radiological data cannot distinguish between PD-L1 targets on the cancer cells and that on the immune cells. In embodiments of the present method, such data can be correlated with microscopy (pathology) images of tissue stained for PD-L1, in a manner analogous to that described above with respect to SUV image data. The PD-L1 PET images can thus be corrected for the expression on cancer cells, which is clinically the relevant parameter.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

The invention claimed is:

1. A computer-implemented method for calibrating radiological data associated with a tissue in a subject, the method comprising the processor-executed steps of:
   analyzing a radiological image of the tissue to calculate a raw value indicative of a biological parameter in the tissue;
   analyzing a microscopy image of the tissue to identify a distribution of cells of interest within the tissue; and
   calculating a calibrated value indicative of a biological parameter of cells of interest within the tissue, wherein the calibrated value is obtained by correcting the raw value based on the identified distribution of cells of interest within the tissue.

2. A method according to claim 1, wherein the biological parameter comprises metabolic activity.

3. A method according to claim 2, wherein the method comprises the processor-executed steps of:
   analyzing the radiological image of the tissue to calculate raw values indicative of metabolic activity at a plurality of locations in the tissue;
   associating the plurality of locations in the tissue with the distribution of the cells of interest identified by analyzing the microscopy image; and
   calculating calibrated values indicative of metabolic activity of cells of interest at the plurality of locations in the tissue, wherein the calibrated values are obtained by correcting the raw values based on the identified distribution of cells of interest at each of the plurality of locations in the tissue.

4. A method according to claim 3, further comprising modifying the radiological image to show the calibrated values indicative of metabolic activity of cells of interest at the plurality of locations in the tissue.

5. A method according to claim 1, wherein the tissue is suspected to comprise cancer cells.

6. A method according to claim 5, wherein the cells of interest comprise cancer cells and/or effector T cells.

7. A method according to claim 1, wherein the radiological image is obtained by positron emission tomography (PET), magnetic resonance imaging (MRI), computerized tomography (CT), or single-photon emission computed tomography (SPECT), or some combination thereof.

8. A method according to claim 7, wherein the raw value indicative of metabolic activity in the tissue is a standard uptake value (SUV) obtained by PET imaging using (18-F) fluorodeoxyglucose (FDG).

9. A method according to claim 1, wherein the microscopy image is obtained by histochemical and/or immunohistochemical staining of a biopsy or resected tissue sample from the tissue.

10. A method according to claim 1, wherein the method comprises calculating a density of cells of interest in the tissue from the cell distribution identified by analyzing the microscopy image, and calculating the calibrated value indicative of a biological parameter of cells of interest by correcting the raw value based on the cell density.

11. A method according to claim 1, wherein the cells of interest comprise cancer cells that overexpress programmed death-ligand 1 (PD-L1).

12. A method according to claim 1, wherein the biological parameter comprises expression of a cellular marker.

13. A method according to claim 12, wherein e.g. the cellular marker is PD-L1.

14. A system for calibrating radiological data associated with a tissue in a subject, the system comprising:
   an interface for receiving a radiological image of the tissue and a microscopy image of the tissue;
   a memory; and
   a processor configured to execute instructions stored on the memory to:
   (i) calculate a raw value indicative of a biological parameter in the tissue from the radiological image;
   (ii) identify a distribution of cells of interest within the tissue from the microscopy image; and
   (iii) calculate a calibrated value indicative of a biological parameter of cells of interest within the tissue, by correcting the raw value based on the identified distribution of cells of interest within the tissue.

15. A computer program product comprising a non-transitory computer readable medium, the computer readable medium having computer readable code embodied therein, the computer readable code being configured such that, on execution by a suitable computer or processor, the computer or processor is caused to perform the method of claim 1.

16. The computer program product according to claim 15, wherein the processor is in communication with a radiological imaging system and/or a microscopy imaging system, and wherein calculating a calibrated value indicative of a biological parameter of cells of interest within the tissue is an improvement to a radiological imaging system.

17. The computer program product according to claim 15, wherein the method is applied to immunotherapy with checkpoint inhibitors or prediction of response to therapy.

18. The computer program product according to claim 15, wherein cell features are detected from trained deep learning algorithm to identify the cells of interest.

19. The computer program product according to claim 15, wherein a spatial correlation of pathology and radiology images is improved, thereby improving image registration between radiological imaging systems and microscopy imaging systems.

20. The computer program product according to claim 15, wherein coordinates of biopsy locations are stored to associate a location of the cells of interest in a radiology image with a corresponding location of the cells of interest in a microscopy image, and therefore the distribution of the cells of interest at such location.

* * * * *